United States Patent
McConnell

(10) Patent No.: US 11,612,724 B2
(45) Date of Patent: Mar. 28, 2023

(54) PINCH-LOCK SHEATH RETENTION MECHANISM

(71) Applicant: BOSTON SCIENTIFIC SCIMED, INC., Maple Grove, MN (US)

(72) Inventor: Kevin McConnell, Saint Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 286 days.

(21) Appl. No.: 16/811,296

(22) Filed: Mar. 6, 2020

(65) Prior Publication Data
US 2020/0282183 A1    Sep. 10, 2020

Related U.S. Application Data

(60) Provisional application No. 62/815,457, filed on Mar. 8, 2019.

(51) Int. Cl.
*A61M 25/00* (2006.01)
*A61M 25/06* (2006.01)
*A61M 25/09* (2006.01)

(52) U.S. Cl.
CPC .... *A61M 25/0662* (2013.01); *A61M 25/0625* (2013.01); *A61M 2025/0681* (2013.01); *A61M 2025/09125* (2013.01)

(58) Field of Classification Search
CPC ... A61M 2025/09125; A61B 2017/347; H02G 15/18; H02G 15/196
See application file for complete search history.

(56) References Cited

U.S. PATENT DOCUMENTS 3,342,179 A    9/1967  Ellmann
4,875,489 A *  10/1989  Messner ........... A61M 25/0905
                                                    604/528

(Continued)

FOREIGN PATENT DOCUMENTS

JP    H0258749 B2 * 12/1990
JP    2016202711 A    12/2016
WO    2007070797 A2    6/2007

OTHER PUBLICATIONS

PCT Application No. PCT/US2017/061779 International Search Report and Written Opinion, dated Feb. 26, 2018.

(Continued)

*Primary Examiner* — William R Carpenter
(74) *Attorney, Agent, or Firm* — Seager, Tufte & Wickhem LLP

(57) ABSTRACT

A medical device system may include a sheath, a pusher wire, and a locking element. The sheath may have a first outer diameter adjacent to the proximal end and an enlarged outer diameter region having a second outer diameter greater than the first adjacent to the intermediate region. The pusher wire may be slidably disposed within a lumen of the sheath. The locking element may have a lumen extending therethrough. The locking element may have a first inner diameter adjacent to the distal end and a second inner diameter smaller than the first adjacent to the intermediate region. The locking element may configured to freely slide over a region of the sheath having the first diameter. When the locking element is disposed over the enlarged outer diameter region of the sheath having the second outer diameter, the locking element may be configured to depress the sheath radially inwards.

15 Claims, 12 Drawing Sheets

(56) References Cited

U.S. PATENT DOCUMENTS

| | | | |
|---|---|---|---|
| 5,117,839 A | 6/1992 | Dance | |
| 5,250,071 A | 10/1993 | Palermo | |
| 5,282,478 A | 2/1994 | Fleischhaker et al. | |
| 5,304,195 A | 4/1994 | Twyford et al. | |
| 5,421,348 A * | 6/1995 | Larnard | A61M 25/0905 |
| | | | 600/585 |
| 5,546,958 A | 8/1996 | Thorud et al. | |
| 5,851,189 A * | 12/1998 | Forber | A61M 25/09041 |
| | | | 604/528 |
| RE37,117 E | 3/2001 | Palermo | |
| 6,491,646 B1 | 12/2002 | Blackledge | |
| 8,568,416 B2 | 10/2013 | Schmitz et al. | |
| 9,320,618 B2 | 4/2016 | Schmitz et al. | |
| 10,441,753 B2 * | 10/2019 | Ellingwood | A61M 25/0069 |
| 2002/0022800 A1 | 2/2002 | O'Holloran et al. | |
| 2004/0225286 A1 * | 11/2004 | Elliott | A61B 18/1477 |
| | | | 606/41 |
| 2005/0119675 A1 | 6/2005 | Adams et al. | |
| 2007/0083219 A1 | 4/2007 | Buiser et al. | |
| 2007/0208276 A1 | 9/2007 | Kornkven et al. | |
| 2007/0282373 A1 | 12/2007 | Ashby et al. | |
| 2008/0109059 A1 | 5/2008 | Gordon et al. | |
| 2008/0119891 A1 | 5/2008 | Miles et al. | |
| 2008/0275458 A1 | 11/2008 | Bleich et al. | |
| 2008/0300616 A1 | 12/2008 | Que et al. | |
| 2009/0043331 A1 | 2/2009 | Buiser et al. | |
| 2009/0125059 A1 * | 5/2009 | Verzal | A61N 1/057 |
| | | | 607/116 |
| 2011/0046657 A1 | 2/2011 | Guo et al. | |
| 2012/0046687 A1 | 2/2012 | Trommeter et al. | |
| 2012/0071856 A1 * | 3/2012 | Goldfarb | A61M 29/00 |
| | | | 604/514 |
| 2012/0177436 A1 | 7/2012 | Lambombard | |
| 2014/0301699 A1 * | 10/2014 | Goldfarb | G02B 6/241 |
| | | | 385/88 |
| 2015/0250470 A1 | 9/2015 | Vargas | |
| 2015/0335333 A1 | 11/2015 | Jones et al. | |
| 2016/0228123 A1 | 8/2016 | Anderson et al. | |
| 2018/0326197 A1 * | 11/2018 | McArthur | A61M 25/09041 |

OTHER PUBLICATIONS

International Preliminary Report on Patentability for PCT Application No. PCT/US2017/061779 dated May 31, 2019, 7 pages.
International Search Report and Written Opinion dated Jul. 1, 2020 for International Application No. PCT/US2020/021428.

* cited by examiner

PINCH-LOCK SHEATH RETENTION MECHANISM

CROSS-REFERENCE TO RELATED APPLICATIONS

This application claims the benefit of priority of U.S. Provisional Application No. 62/815,457 filed Mar. 8, 2019, the entire disclosure of which is hereby incorporated by reference.

TECHNICAL FIELD

The present disclosure pertains to medical devices and methods for manufacturing and/or using medical devices. More particularly, the present disclosure pertains to configurations of a system for securing a medical device within a sheath.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first example, a medical device system may comprise a sheath having a proximal end, a distal end, an intermediate region disposed between the proximal end and the distal end, and a lumen extending from the proximal end to the distal end. The sheath may have a first outer diameter adjacent to the proximal end and an enlarged outer diameter region having a second outer diameter adjacent to the intermediate region, the second outer diameter greater than the first outer diameter. A pusher wire may be slidably disposed within the lumen of the sheath. A locking element may have a proximal end, a distal end, and an intermediate region disposed between the proximal end and the distal end, and a lumen extending from the proximal end to the distal end. The locking element may have a first inner diameter adjacent to the distal end and a second inner diameter adjacent to the intermediate region, the second inner diameter smaller than the first outer diameter. The locking element may be configured to freely slide over a region of the sheath having the first diameter and when the locking element is disposed over the enlarged outer diameter region of the sheath having the second outer diameter, the locking element may be configured to depress the sheath radially inwards.

Alternatively or additionally to any of the examples above, in another example, when the locking element is disposed over the enlarged outer diameter region of the sheath, an inner surface of the sheath may frictionally engage an outer surface of the pusher wire.

Alternatively or additionally to any of the examples above, in another example, the second inner diameter and the first inner diameter may be coupled by flared surface.

Alternatively or additionally to any of the examples above, in another example, the second inner diameter may extend over less than an entire length of the locking element.

Alternatively or additionally to any of the examples above, in another example, the lumen of the locking element may have a generally hourglass shape.

Alternatively or additionally to any of the examples above, in another example, a cross-sectional shape of the lumen of the locking element may be a same shape along a length of the lumen.

Alternatively or additionally to any of the examples above, in another example, the cross-sectional shape of the lumen of the locking element may be circular.

Alternatively or additionally to any of the examples above, in another example, the cross-sectional shape of the lumen of the locking element may be ellipsoid.

Alternatively or additionally to any of the examples above, in another example, a cross-sectional shape of the lumen of the locking element may vary along a length of the lumen.

Alternatively or additionally to any of the examples above, in another example, the cross-sectional shape of the lumen of the locking element may be circular adjacent to the proximal end and the distal end and the cross-sectional shape of the lumen of the locking element may be ellipsoid adjacent to the intermediate region.

Alternatively or additionally to any of the examples above, in another example, the enlarged outer diameter region of the sheath may extend along less than an entire length of the sheath.

Alternatively or additionally to any of the examples above, in another example, the enlarged outer diameter region of the sheath may comprise a proximal waist, an intermediate region, and a distal waist.

Alternatively or additionally to any of the examples above, in another example, the proximal waist may be configured to gradually transition an outer diameter of the sheath from the first outer diameter to the second outer diameter.

Alternatively or additionally to any of the examples above, in another example, an inner diameter of the sheath may be constant from the proximal end to the distal end.

Alternatively or additionally to any of the examples above, in another example, the locking element may be formed from a more rigid material than the sheath.

In another example, a medical device system may comprise a sheath having a proximal end, a distal end, an intermediate region disposed between the proximal end and the distal end, and a lumen extending from the proximal end to the distal end. The sheath may have a first outer diameter adjacent to the proximal end and an enlarged outer diameter region having a proximal waist, an intermediate region having a second outer diameter greater than the first outer diameter, and a distal waist. A pusher wire may be slidably disposed within the lumen of the sheath. A locking element may have a proximal end, a distal end, and an intermediate region disposed between the proximal end and the distal end, and a lumen extending from the proximal end to the distal end. The lumen of the locking element may have a generally hourglass shape including a smaller inner diameter adjacent the intermediate region than at the proximal or distal end. The locking element may be configured to freely slide over a region of the sheath having the first diameter and when the locking element is disposed over the enlarged outer diameter region of the sheath having the second outer diameter, the locking element may be configured to depress the sheath such that an inner surface of the sheath is depressed radially inwards and frictionally engages an outer surface of the pusher wire.

Alternatively or additionally to any of the examples above, in another example, a cross-sectional shape of the lumen of the locking element may be a same shape along a length of the lumen.

Alternatively or additionally to any of the examples above, in another example, a cross-sectional shape of the lumen of the locking element may vary along a length of the lumen.

Alternatively or additionally to any of the examples above, in another example, the locking element may be formed from a more rigid material than the sheath.

Alternatively or additionally to any of the examples above, in another example, the system may further comprise an implant releasably coupled to the pusher wire.

In another example, a method for inhibiting movement between a wire and a sheath may comprise inserting a wire into a lumen of a tubular sheath, the tubular sheath may have a localized region of increased outer diameter and sliding a locking element distally over an outer diameter of the tubular sheath until the locking element may be disposed over the localized region of increased outer diameter, the locking element configured to freely slide over a proximal end region of the tubular sheath. the locking element may be configured to depress the tubular sheath radially inwards when the locking element is disposed over the localized region of increased outer diameter and when the locking element is disposed over the localized region of increased outer diameter of the tubular sheath, an inner surface of the tubular sheath may frictionally engage an outer surface of the wire.

Alternatively or additionally to any of the examples above, in another example, distally advancing the locking element distally beyond the localized region of increased outer diameter of the tubular sheath may remove the radially inward force from the tubular sheath.

Alternatively or additionally to any of the examples above, in another example, the locking element may be formed from a more rigid material than the tubular sheath.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
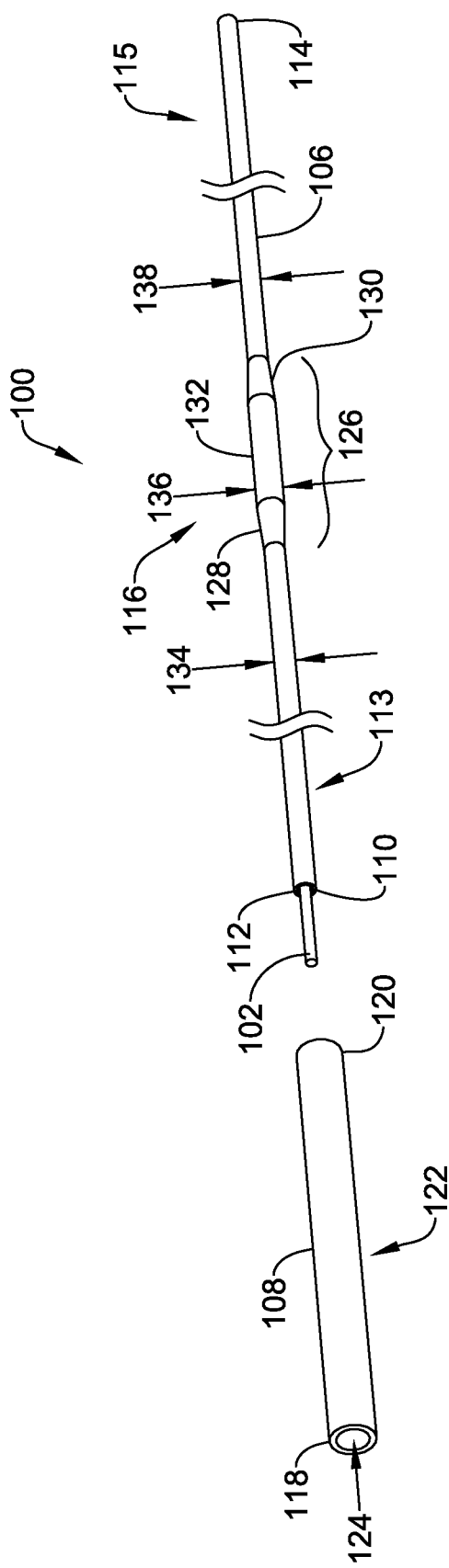
FIG. 1 is a perspective view of an example medical device system in a first configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

FIG. 1 is a perspective view of an example medical device system 100 in a partially unassembled configuration. The medical device system 100 may include a pusher wire 102, an implant 104 (see, for example, FIGS. 6 and 8), such as, but not limited to an embolic coil, an introducer sheath 106, and a locking element 108. For simplicity, the implant 104 is described as an embolic coil, but other suitable medical devices transported, delivered, used, released, etc. in a similar manner are also contemplated, including but not limited to, vascular occlusion devices coils, stents, embolic filters, replacement heart valves, other occlusion devices, and/or other medical implants, etc.

Embolic coils 104 may be typically introduced into a blood vessel by using a microcatheter (not explicitly shown) that extends from a proximal point outside the patient's body to a distal point near the embolization site. An introducer sheath 106 containing the coil 104 can be used to carry and protect the coil 104 prior to insertion into the patient. Further, the introducer sheath 106 may be used to transfer the coil to the microcatheter and/or to assist in deploying the coil at a selected embolization site. The sheath 106 may be configured to protect the implant 104 and maintain the implant 104 in a deliverable orientation, until the implant 104 is deployed. As will be described in more detail herein, the locking element 108 may be configured to limit movement (e.g., axial and rotational) of the pusher wire 102 and implant 104 within the sheath 106 until the user is ready to advance the implant 104 out of the sheath 106.

The sheath 106 may be a tubular member including a proximal end 112, a distal end 114, and an intermediate region 116 positioned therebetween. Some suitable but non-limiting materials for the sheath 106, for example, polymer materials, composite materials, etc., are described below. The sheath 106 may define a lumen 110 extending from the proximal end 112 to the distal end 114. The pusher wire 102 and implant 104 may be slidably disposed within the lumen 110 of the sheath 106 such that the pusher wire 102 and the implant 104 are radially inwards of the sheath 106. The implant 104 may be disposed proximate the distal end 114 of the sheath 106. The pusher wire 102 may be axially slidable between an interlocked position and a released position. The pusher wire 102 may be configured to be releasably attached to the implant 104. The implant 104 may be configured to expand from a delivery configuration to a deployed configuration. The pusher wire 102 may generally be a solid wire or shaft, but may also be tubular in some embodiments. Some suitable but non-limiting materials for the pusher wire 102, for example metallic materials, polymer materials, composite materials, etc., are described below. As will be described in more detail herein, the pusher wire 102 may be releasably secured to the sheath 106 via the locking element 108 to limit axial and/or rotationally movement of the pusher wire 102 within the sheath 106.

The sheath 106 may have a localized bump or enlarged outer diameter region 126 within the intermediate region 116 which extends less than an entire length of the sheath 106 while the inner diameter remains constant as will be discussed in more detail herein. It is contemplated that the sheath 106 may be formed as a single unitary structure or may be formed from separate components coupled together, as desired. For example, the sheath 106 may be extruded or molded as a single piece. In other cases, a constant diameter sheath 106 may be formed and the enlarged outer diameter region 126 formed over the constant diameter tubular member (e.g., reflowing). It is contemplated that the sheath 106 may be formed from a single material or a combination of materials, as desired. In some cases, the enlarged outer diameter region 126 may formed from a material having different properties (e.g., softer, harder, etc.) from the remaining portions of the sheath 106.

In some cases, the enlarged outer diameter region 126 may be positioned closer to the proximal end 112 than the distal end 114, although this is not required. The enlarged outer diameter region 126 may have a proximal waist 128, a distal waist 130, and an intermediate portion 132 positioned between the proximal waist 128 and the distal waist 130. In some cases, the enlarged outer diameter region 126 may be formed from different materials. For example, the intermediate portion 132 may be softer or harder than one or both of the waists 128, 130. The is just an example. Other material combinations and configuration may be used, as desired. The proximal waist 128 may increase in outer diameter in the distal direction from a first outer diameter 134 to a second outer diameter 136. It is contemplated that the change from the first outer diameter 134 to the second outer diameter 136 may be gradual and sloping, or may be abrupt and step-wise, as desired. It is contemplated that a tapered, ramp-like gradual change at the proximal waist 128 may facilitate positioning of the locking element 108, but this is not required. The distal waist may decrease in outer diameter in the distal direction from the second outer diameter 136 to a third outer diameter 138. It is contemplated that the change from the second outer diameter 136 to the third outer diameter 138 may be gradual and sloping, or may be abrupt and step-wise, as desired. It is contemplated that a tapered, ramp-like gradual change at the distal waist 130 may facilitate positioning of the locking element 108, but this is not required. In some instances, the first and third outer diameters 134, 138 may be substantially the same, although this is not required. For example, the sheath 106 may have a generally constant outer diameter from the proximal end 112 to the distal end 114 with the exception of the enlarged outer diameter region 126. Said differently, the sheath 106 may have a first, or proximal end region 113 extending from the proximal end 112 to the proximal waist 128 and having a relatively constant outer diameter 134 and a second, or distal end region 115 extending from the distal waist 130 to the distal end 114 and having a relatively constant outer diameter 138 which is approximately equal to the first outer diameter 134. However, configurations where either the proximal end region 113 or the distal end region 115 have a larger outer diameter than the other are also contemplated.

Figure 2:
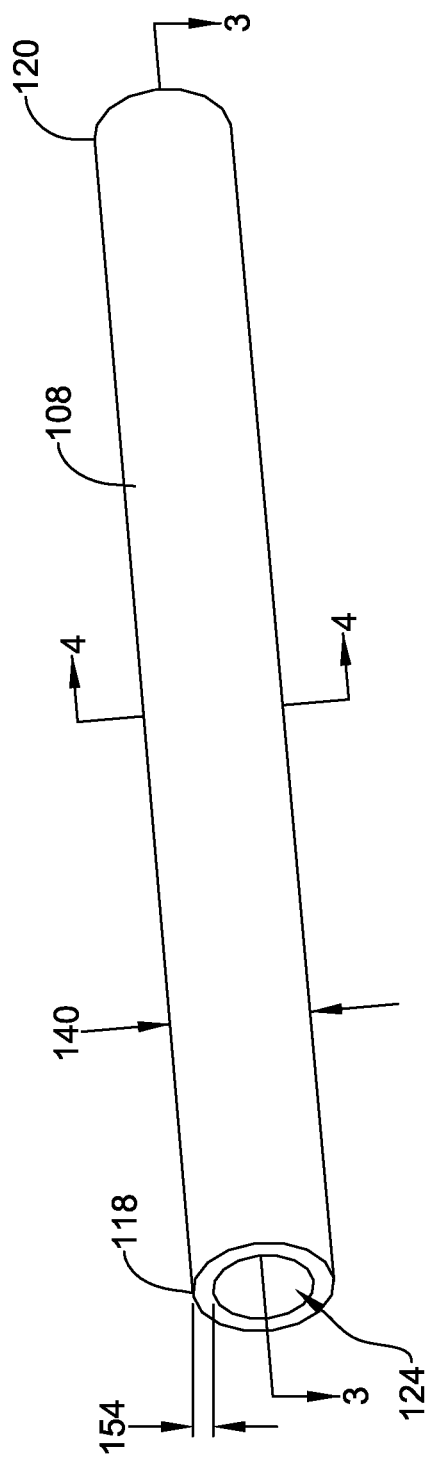
FIG. 2 is a perspective view of an illustrative locking mechanism.
Figure 5:
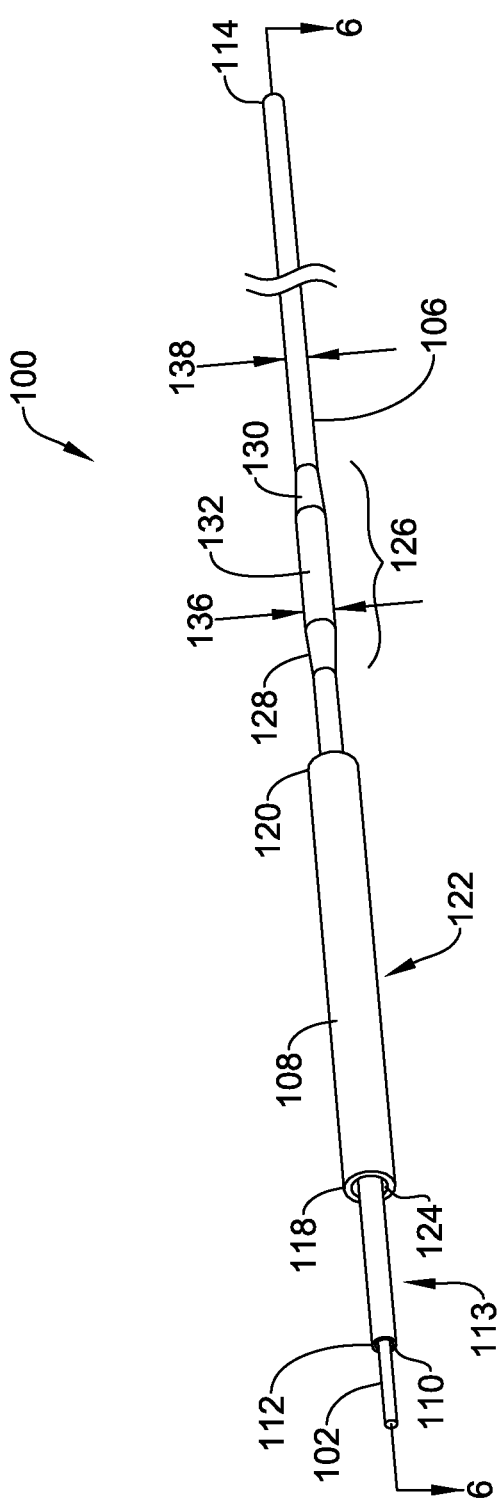
FIG. 5 is a perspective view of the illustrative medical device system of FIG. 1 in a second configuration.
Figure 6:
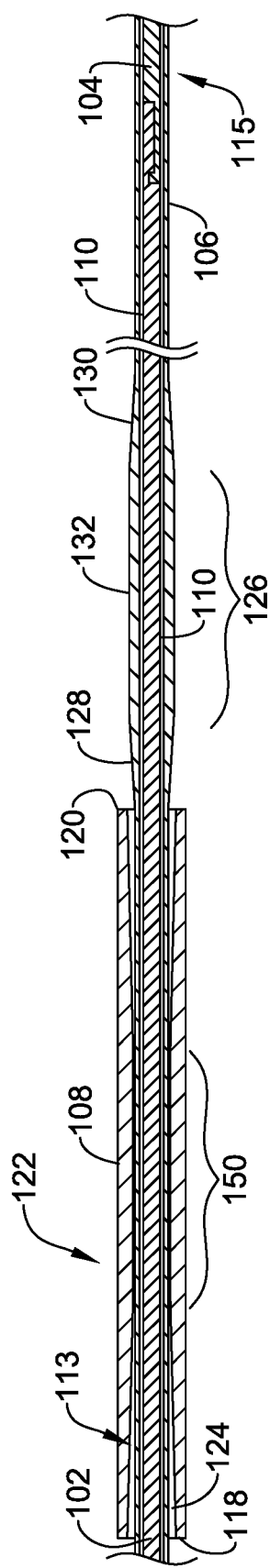
FIG. 6 is a partial cross-sectional view of the illustrative medical device system of FIG. 5.

Referring additionally to FIG. 2, which illustrates a perspective view of the locking element 108, the locking element 108 may be a tubular member having a proximal end 118, a distal end 120, and an intermediate region 122 positioned therebetween. The locking element 108 may have a generally constant or uniform outer diameter 140 from the proximal end 118 to the distal end 120, although this is not required. The locking element 108 may define a lumen 124 extending from the proximal end 118 to the distal end 120. As will be discussed in more detail herein, the lumen 124 of the locking element 108 may be sized to slide freely over at least proximal end region 113 of the sheath 106, as shown in FIGS. 5 and 6. The lumen 124 of the locking element 108 may also be sized to slide freely over at least a region of the sheath 106 distal to the enlarged diameter region 126. Thus, in some configurations, at least a portion of the sheath 106 may be radially inward of the locking element 108.

Figure 3:
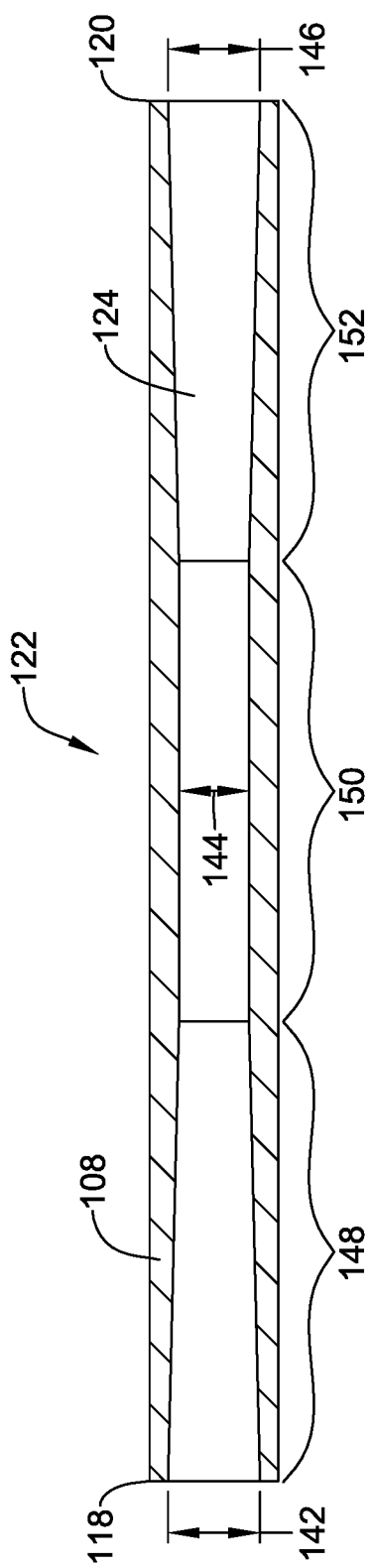
FIG. 3 is a cross-sectional view of the illustrative locking mechanism of FIG. 2.

FIG. 3 is a cross-sectional view of the locking element 108 taken at line 3-3 of FIG. 2. The locking element 108 may have a variable inner diameter. In some embodiments, the locking element 108 may have an hourglass shape such that the inner diameter tapers from a larger inner diameter 142, 146 adjacent to the proximal and distal ends 118, 120, respectively, to a smaller inner diameter 144 adjacent to the intermediate region 122 of the locking element 108. For example, the inner diameter may taper gradually from a first inner diameter 142 adjacent to the proximal end 118 to the second smaller inner diameter 144 over a proximal length 148 of the locking element 108. In other embodiments, the transition from the first inner diameter 142 to the second inner diameter may be a step-wise or abrupt transition. The second or smaller inner diameter 144 may be approximately constant or uniform over a second or central length 150 of the locking element. The inner diameter may flare gradually from a second smaller inner diameter 144 to the larger third inner diameter 146 adjacent to the distal end 120 over a distal length 152 of the locking element 108. In other embodiments, the transition from the second inner diameter 144 to the third inner diameter 146 may be a step-wise or abrupt transition. In some embodiments, the central length 150 of the locking element 108 having the reduced inner diameter 144 may be approximately the same as a length of the intermediate portion 132 of the enlarged outer diameter region 126 of the sheath 106, although this is not required. The second, smaller inner diameter 144 may be sized such that the locking element 108 can slide freely over the proximal end region 113 and/or distal end region 115 of the sheath 106.

Figure 4:
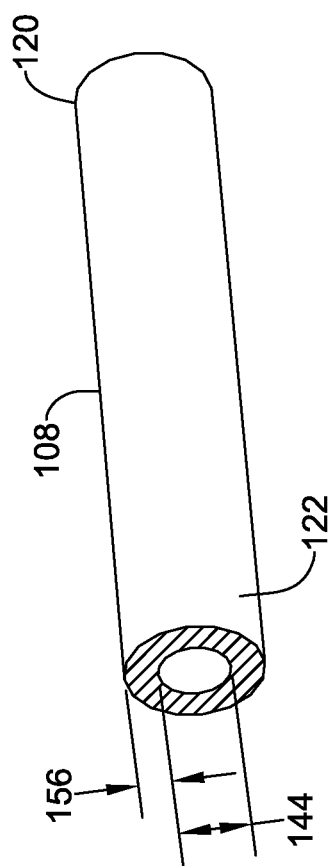
FIG. 4 is another cross-sectional view of the illustrative locking mechanism of FIG. 2.

In some embodiments, the inner diameter of the locking element 108 is varied while the cross-sectional shape of the lumen 124 remains the same. For example, referring additionally to FIG. 4 which illustrates a cross-sectional view of the locking element 108 taken at line 4-4 of FIG. 2, the lumen 124 may have a generally circular cross-sectional shape adjacent to the proximal end 118 and a generally circular cross-sectional shape adjacent to the intermediate region 122. However, the wall thickness of the locking element 108 varies inversely with the inner diameter. For example, the locking element 108 may have a first wall thickness 154 adjacent to the proximal end and a second, greater, wall thickness 156 adjacent to the intermediate region 122.

It is contemplated that the configuration of the locking element 108 may be adjusted to create the desired effect. For example, one or more of the inner diameter 142, 144, 146 may be made larger or smaller to accommodate different sizes of sheaths 106. Further, the proximal and/or distal lengths 148, 152 may be longer, shorter, less angled, more angled, etc. In another example, the outer diameter of the locking element 108 may be increased or decreased to facilitate handling. It is further contemplated that the outer surface of the locking element 108 may include features to improve ergonomic handling, such as, but not limited to, bumps, waves, texturing, or indentations to improve gripability. In some cases, the sheath 106 and/or the locking element 108 may include visual indicia to guide the user in manipulation of the locking element 108. In some cases, the central length 150 and/or the overall length of the locking element 108 can be increased or decreased, as desired.

FIG. 5 is a perspective view of the illustrative medical device system 100 in an unlocked or first assembled configuration and FIG. 6 is a partial cross-sectional view of the illustrative medical device system 100, taken at line 6-6 of FIG. 5. From the partially unassembled configuration illustrated in FIG. 1, to position the locking element 108 such that it can be used to secure the pusher wire 102, the locking element 108 is distally advanced over the proximal end region 113 of the sheath 106 from the proximal end 112. In this configuration, the pusher wire 102 is free to slide axially (e.g., proximally and distally) and/or rotate within the lumen 110 of the sheath 106. As described above, the inner diameter of the sheath 106 may remain constant, or substantially constant from the proximal end 112 to the distal end 114. The wall thickness of the enlarged outer diameter region 126 may be greater than the wall thickness of the proximal end region 113 and/or the distal end region 115 to create the localized bump.

Figure 7:
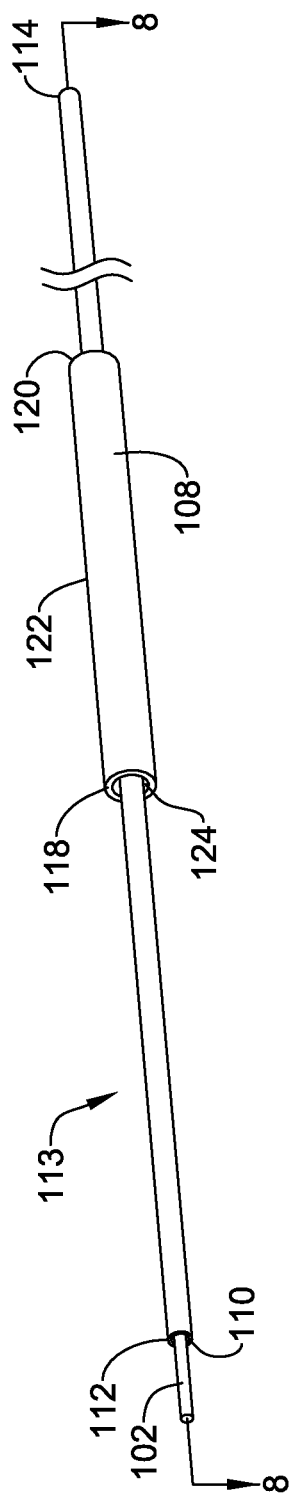
FIG. 7 is a perspective view of the illustrative medical device system of FIGS. 1 and 5 in a third configuration.
Figure 8:
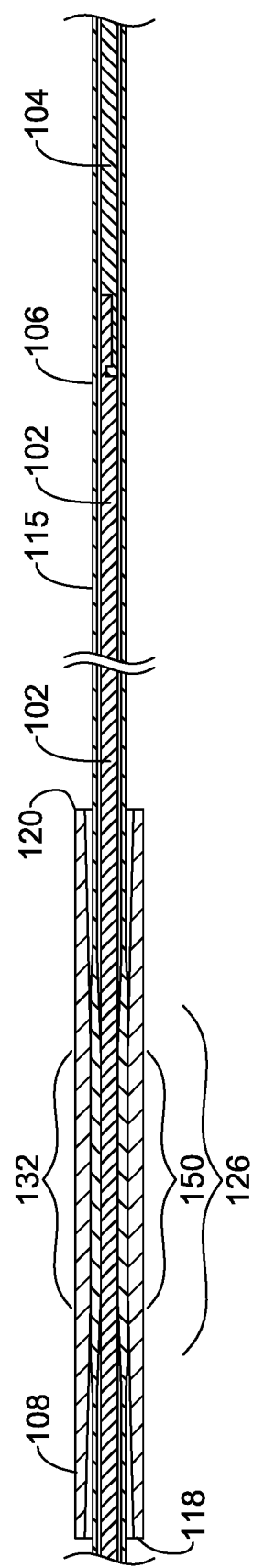
FIG. 8 is a partial cross-sectional view of the illustrative medical device system of FIG. 7.

To lock the pusher wire 102 relative to the sheath, the locking element 108 is advanced further in the distal direction until the central length 150 of the locking element 108 is disposed over the intermediate region 132 of the enlarged outer diameter region 126 of the sheath 106. While FIG. 5 illustrates the locking element 108 as proximal to the enlarged diameter portion 126, in some cases the locking element 108 may be initially positioned distal to the enlarged diameter region 126. In such an instance, the locking element 108 may be proximally retracted to bring the locking element 108 into the locked configured (e.g., positioned over the enlarged diameter region 126). FIG. 7 is a perspective view of the illustrative medical device system 100 in a locked or second assembled configuration and FIG. 8 is a partial cross-sectional view of the illustrative medical device system 100, taken at line 8-8 of FIG. 7. As described above, the locking element 108 may slide freely over the proximal end region 113 (and/or the distal end region 115) of the sheath. When the locking element 108 reaches enlarged outer diameter region 126, the enlarged outer diameter region 126 of the sheath 106 may be depressed to allow the locking element 108 to advance over the enlarged outer diameter region 126. The locking element 108 may pinch or exert a radially inward biasing force on an outer surface of the enlarged outer diameter region 126 such that the outer diameter of the enlarged outer diameter region 126 is decreased and the inner diameter of the enlarged outer diameter region 126 is biased radially inward, as shown in FIG. 8. As the inner diameter of the enlarged outer diameter region 126 is reduced, the intermediate portion 132 contacts and frictionally engages an outer surface of the pusher wire 102. In the locked configuration illustrated in FIGS. 7 and 8, the frictional engagement between the inner surface of the sheath 106 and the outer surface of the pusher wire 102 may preclude or inhibit axial (e.g., proximally and distally) and/or rotational movement of the pusher wire 102 within the lumen 110 of the sheath 106. In some embodiments, the enlarged outer diameter region 126 may include features to promote inward deflection thereof. For example, the enlarged outer diameter region 126 may include slots formed therein. In one embodiments, two slots may be formed approximately 180 degrees apart to promote deflection. This is just an example. Fewer than two slots or more than two slots may be provided to facilitate deflection, as desired. Further, the slots may be uniformly or eccentrically distributed about a circumference of the enlarged outer diameter region 126.

It is contemplated that the gradual increase in the outer diameter of the proximal waist 128 of the enlarged outer diameter region 126 and the gradual decrease in the inner diameter of the proximal length 148 of the locking element 108 may facilitate positioning of the locking element 108 over the enlarged outer diameter region 126 as the locking element 108 is moved in the distal direction. The slopes of the distal waist 130 and the distal length 152 may similarly facilitate proximal movement of the locking element 108 from a location distal to the enlarged outer diameter region 126. When the user is ready to advance the implant 104, the locking element 108 may be advanced distally or removed proximally from the enlarged outer diameter region 126. This may allow the inner diameter of the sheath 106 adjacent to the enlarged outer diameter region 126 to expand to the original configuration and the pusher wire 102 to move freely. Thus, as the sheath 106 is removed from the pusher wire 102, the sheath 106 does not engage or hang up on any portion of the pusher wire 102.

It is contemplated that the outer diameter 136 of the intermediate portion 132 of the enlarged outer diameter region 126 and the inner diameter 144 of the central length 150 of the locking element 108 may be selected such that the enlarged outer diameter region 126 is capable of contacting the pusher wire 102 when the locking element 108 is in the locked configuration (e.g., disposed over the enlarged outer diameter region 126). For example, a pusher wire 102 may have an outer diameter of about 0.016 inches (0.406 millimeters (mm)) and the sheath 106 may have an inner diameter of about 0.025 inches (0.635 mm). If the outer diameter 134 of the sheath 106 at the proximal end region 113 is about 0.034 inches (0.864 mm), the smallest inner dimeter 144 of the locking element 108 may be about 0.037 inches (0.940 mm) to allow the locking element 108 to slide freely over the proximal end region 113. Thus, the maximum outer diameter 136 of the enlarged outer diameter region 126 may be about 0.046 inches (1.168 mm). Thus, the enlarged outer diameter region 126 would require a 0.009 inch (0.229 mm) reduction in diameter to allow the locking element 108 to pass over. The 0.009 inch (0.229 mm) reduction when transferred to the inner diameter of the sheath 106 would reduce to the inner diameter of the sheath 106 from 0.025 inches (0.635 mm) to 0.016 inches (0.406 mm), which is the outer diameter of the pusher wire 102. This is just one example. The inner and/or outer diameters of the locking element 108 and/or sheath 106 can be varied to accommodate the diameter of the wire or other component to be secured.

It is further contemplated that that locking element 108 may be formed from a material that is more rigid than or stiffer than the outer sheath 106. For example, the material for the locking element 108 may be selected such that the locking element does not deflect when the locking element 108 is advanced over the enlarged outer diameter portion 126 but rather forces the sheath 106 to deflect inward. In some cases, the locking element 108 may be injection molded, 3D-printed, etc. In some embodiments, the locking element 108 may be formed from a bright (or other) color easily noticeable by the user. In some cases, a segment on the outer surface of the sheath 106 approximately equal in length to the locking element 108 and distal to the enlarged outer diameter portion 126 may be made the same color (or a different color, as desried). This may indicate to the user to slide the locking element 108 to overlap the like-colored (or differently colored) segment of the sheath 106, clearly indicated how to actuate the unlocking mechanism. This may also improve clarity on sliding the locking element 108 distally. While not required, sliding the locking element 108 distally may reduce the required travel motion and to avoid having a loose component (e.g., the locking element 108) on the operating table. In some cases, the proximal end region 113 of the sheath 106 may be include an increase in outer diameter (e.g., a mechanical stop point) adjacent the proximal end 112 may be provided to prevent the locking element 108 from separating from the sheath 106 if the locking element 108 is proximally retracted to unlock the components.

Figure 9:
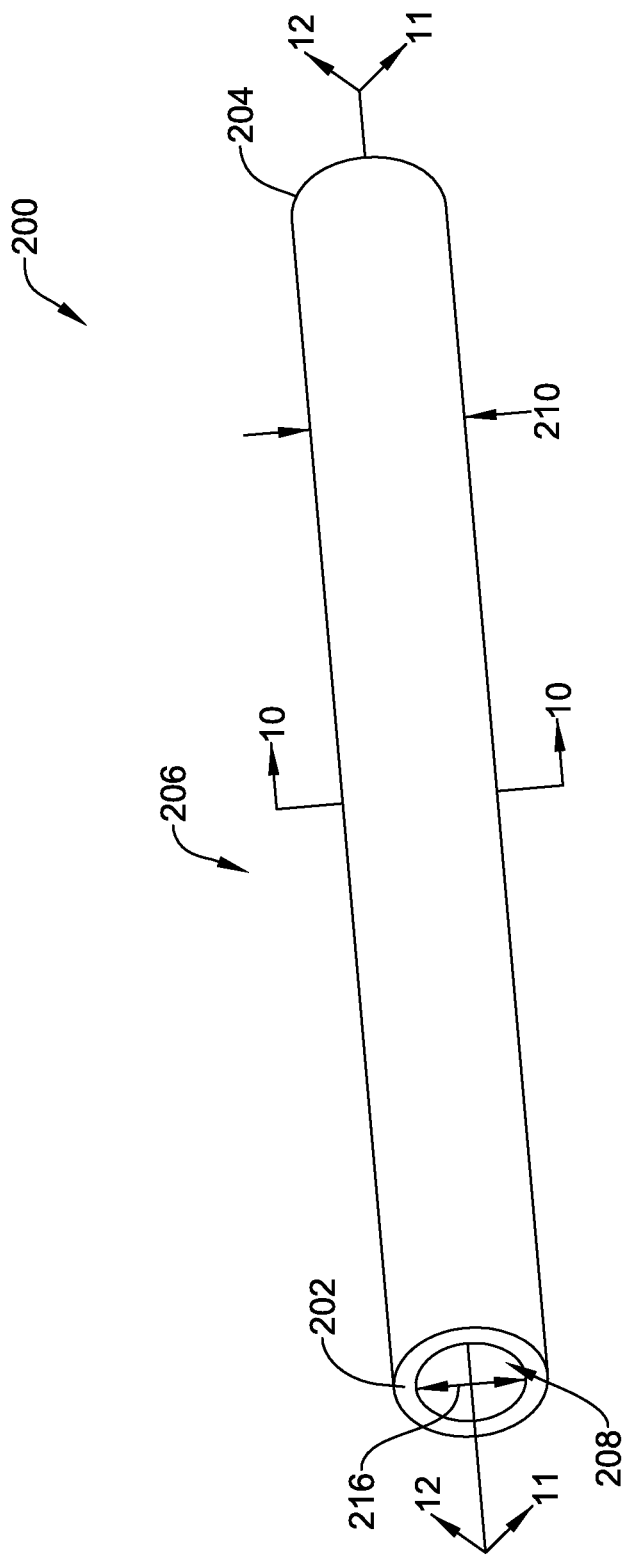
FIG. 9 is a perspective view of another illustrative locking mechanism.

FIG. 9 illustrates a perspective view of another illustrative locking element 200. The locking element 200 may be a tubular member having a proximal end 202, a distal end 204, and an intermediate region 206 positioned therebetween. The locking element 200 may have a generally constant or uniform outer diameter 210 from the proximal end 202 to the distal end 204, although this is not required. The locking element 200 may define a lumen 208 extending from the proximal end 202 to the distal end 204. As described above, the lumen 208 of the locking element 200 may be sized to slide freely over at least a proximal end region of a sheath, such as the sheath 106 described above.

Figure 10:
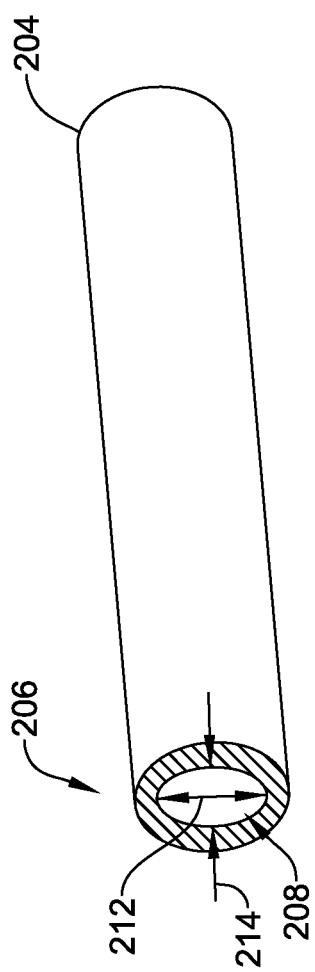
FIG. 10 is a cross-sectional view of the illustrative locking mechanism of FIG. 9.

Similar to the locking element 108 described above, the locking element 200 may have a variable inner diameter. However, in addition to having a smaller inner diameter adjacent to the intermediate region 206, the cross-sectional shape of the lumen 208 may change as the diameter reduces. FIG. 10 is a cross-sectional view of the locking element 200 taken at line 10-10 of FIG. 9. In the illustrated embodiment, the cross-sectional shape may change from circular adjacent to the proximal end 202 and the distal end 204 to ellipsoid adjacent to the intermediate region 206. It is contemplated that the major diameter 212 of the intermediate region 206 may be approximately the same as the inner diameter 216 of the circular cross-section adjacent the proximal end 202 (and/or distal end 204) while the minor diameter 214 of the intermediate region 206 may be smaller than the inner diameter 216 of the circular cross-section adjacent the proximal end 202 (and/or distal end 204). This may change the locking mechanism (of the locking element 200, sheath 106 and pusher wire 102) to a compressive lock at two points around the circumference rather than a hoop stress. In some cases, while not explicitly shown, the cross-sectional shape of the lumen 208 may be ellipsoid from the proximal end 202 to the distal end 204.

Figure 11:
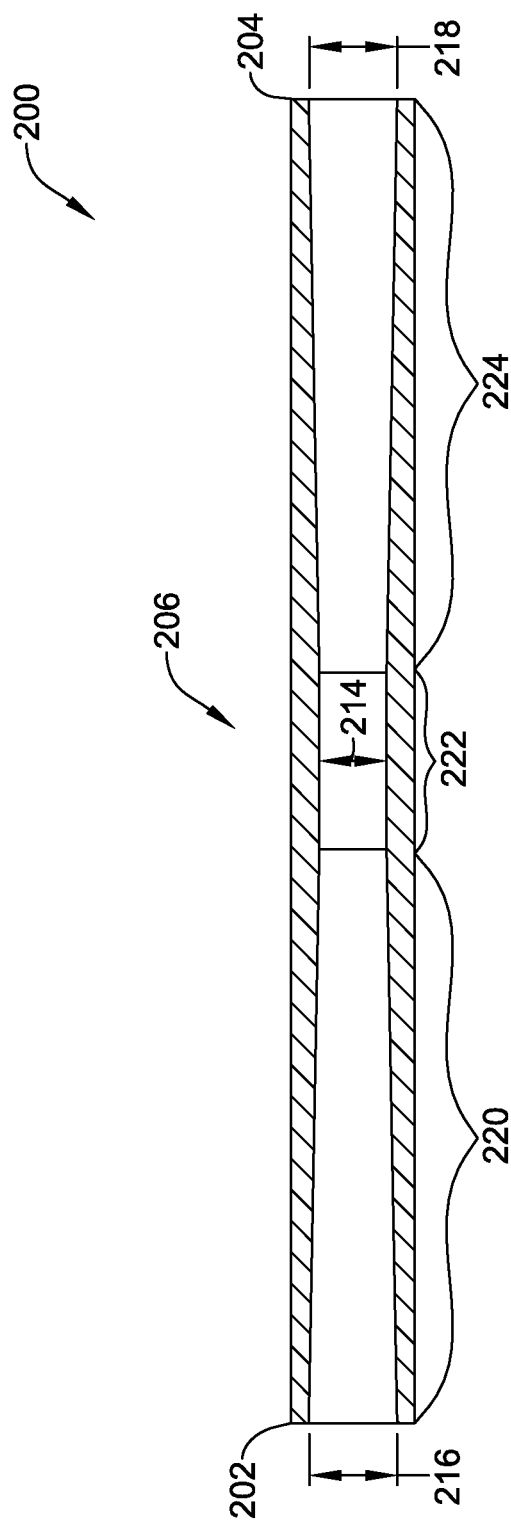
FIG. 11 is another cross-sectional view of the illustrative locking mechanism of FIG. 9.
Figure 12:
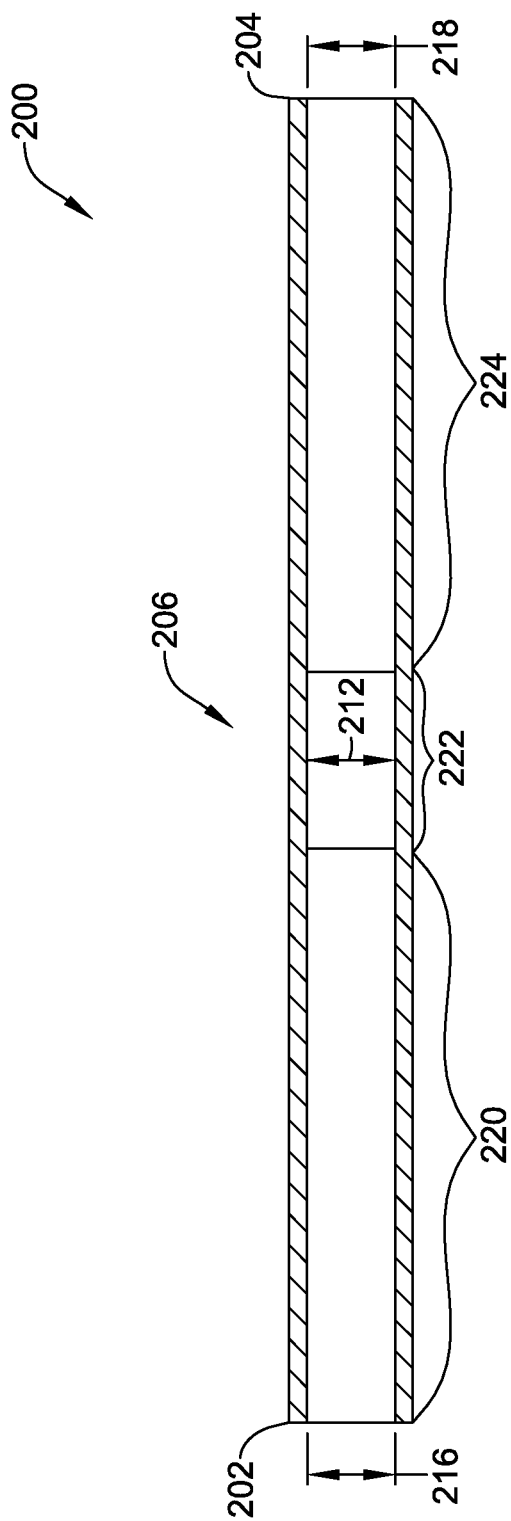
FIG. 12 is another cross-sectional view of the illustrative locking mechanism of FIG. 9.

FIG. 11 is a cross-sectional view of the locking element 200 taken at line 11-11 of FIG. 9. As described above the locking element 200 may have a variable inner diameter. In some embodiments, the locking element 200 may have an hourglass shape that such that the inner diameter tapers in at least one dimension (e.g., the minor axis of the ellipse) from a larger inner diameter 216, 218 adjacent to the proximal and distal ends 202, 204, respectively, to a smaller inner diameter 214 adjacent to the intermediate region 206 of the locking element 200. For example, the inner diameter may taper gradually from a first inner diameter 216 adjacent to the proximal end 202 to the second smaller inner diameter 214 over a proximal length 220 of the locking element 200. In other embodiments, the transition from the first inner diameter 216 to the second inner diameter 214 may be a step-wise or abrupt transition. The second or smaller inner diameter 214 may be approximately constant or uniform over a second or central length 222 of the locking element. The inner diameter may flare gradually from a second smaller inner diameter 214 to the larger third inner diameter 218 adjacent to the distal end 204 over a distal length 224 of the locking element 200. In other embodiments, the transition from the second inner diameter 214 to the third inner diameter 218 may be a step-wise or abrupt transition. In some embodiments, the central length 222 of the locking element 200 having the reduced inner diameter 214 may be approximately the same as a length of the intermediate portion 132 of the enlarged outer diameter region 126 of the sheath 106, although this is not required. The second, smaller inner diameter 214 may be sized such that the locking element 200 can slide freely over the proximal end region 113 and/or distal end region 115 of the sheath 106. As described above, as the shape of the lumen 208 changes, the minor diameter 214 of the ellipse may reduce in size while the major diameter 212. FIG. 12 is a cross-sectional view of the locking element 200 taken at line 12-12 of FIG. 9 illustrating the constant major diameter along a length of the locking element 200.

It is contemplated that the configuration of the locking element 200 may be adjusted to create the desired effect. For example, one or more of the inner diameter 216, 214, 218 may be made larger or smaller to accommodate different sizes of sheaths 106. Further, the proximal and/or distal lengths 220, 224 may be longer, shorter, less angled, more angled, etc. In another example, the outer diameter of the locking element 200 may be increased or decreased to facilitate handling. It is further contemplated that the outer surface of the locking element 200 may include features to improve ergonomic handling, such as, but not limited to, bumps, waves, texturing, or indentations to improve gripability. In some cases, the locking element 200 may include visual indicia to guide the user in manipulation of the locking element 200. In some cases, the central length 222 and/or the overall length of the locking element 200 can be increased or decreased, as desired.

In some embodiments, the medical device system 100, the pusher wire 102, the implant 104, the sheath 106, the locking element 108, 200, and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 100, the pusher wire 102, the implant 104, the sheath 106, the locking element 108, 200, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 100, the pusher wire 102, the implant 104, the sheath 106, and/or components thereof, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 100, the pusher wire 102, the implant 104, the sheath 106, the and/or components thereof, etc. to achieve the same result.

In some embodiments, a degree of Magnetic Resonance Imaging (MRI) compatibility is imparted into the medical device system 100, the pusher wire 102, the implant 104, the sheath 106, the locking element 108, 200, and/or components thereof, etc. For example, the medical device system 100, the pusher wire 102, the implant 104, the sheath 106, the locking element 108, 200, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The the medical device system 100, the pusher wire 102, the implant 104, the sheath 106, the locking element 108, 200, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 100, the pusher wire 102, the implant 104, the sheath 106, the locking element 108, 200, etc. and/or components thereof, and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 100, the pusher wire 102, the implant 104, the sheath 106, the locking element 108, 200, and/or components thereof, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 100, the pusher wire 102, the implant 104, the sheath 106, the locking element 108, 200, and/or components thereof, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 100, the pusher wire 102, the implant 104, the sheath 106, the locking element 108, 200, and/or components thereof, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
   a sheath having a proximal end, a distal end, an intermediate region disposed between the proximal end and the distal end, and a lumen extending from the proximal end to the distal end, the sheath having a first outer diameter adjacent to the proximal end and an enlarged outer diameter region having a second outer diameter adjacent to the intermediate region, the second outer diameter greater than the first outer diameter;
   a pusher wire slidably disposed within the lumen of the sheath; and
   a locking element having a proximal end, a distal end, and an intermediate region disposed between the proximal end and the distal end, and a lumen extending from the proximal end to the distal end, the locking element having a first inner diameter adjacent to the distal end and a second inner diameter adjacent to the intermediate region, the second inner diameter smaller than the first outer diameter;
   wherein the locking element is configured to freely slide over a region of the sheath having the first outer diameter; and
   wherein when the locking element is disposed over the enlarged outer diameter region of the sheath having the second outer diameter, the locking element is configured to depress the intermediate region of the sheath radially inwards at the enlarged outer diameter region;
   wherein a cross-sectional shape of the lumen of the locking element varies along a length of the lumen; and
   wherein the cross-sectional shape of the lumen of the locking element is circular adjacent to the proximal end of the locking element and the distal end of the locking element and the cross-sectional shape of the lumen of the locking element is ellipsoid adjacent to the intermediate region of the locking element.

2. The medical device system of claim 1, wherein when the locking element is disposed over the enlarged outer diameter region of the sheath, an inner surface of the sheath frictionally engages an outer surface of the pusher wire.

3. The medical device system of claim 1, wherein the lumen of the locking element has a generally hourglass shape.

4. The medical device system of claim 1, wherein a cross-sectional shape of the lumen of the locking element is a same shape along a length of the lumen.

5. The medical device system of claim 4, wherein the cross-sectional shape of the lumen of the locking element is circular.

6. The medical device system of claim 4, wherein the cross-sectional shape of the lumen of the locking element is ellipsoid.

7. The medical device system of claim 1, wherein an inner diameter of the sheath is constant from the proximal end to the distal end.

8. The medical device system of claim 7, wherein the proximal waist is configured to gradually transition an outer diameter of the sheath from the first outer diameter to the second outer diameter.

9. The medical device system of claim 1, wherein the enlarged outer diameter region of the sheath comprises a proximal waist, an intermediate portion, and a distal waist.

10. The medical device system of claim 1, wherein the locking element is formed from a more rigid material than the sheath.

11. A medical device system, comprising:
- a sheath having a proximal end, a distal end, an intermediate region disposed between the proximal end and the distal end, and a lumen extending from the proximal end to the distal end;
- the sheath having a first outer diameter adjacent to the proximal end and an enlarged outer diameter region having a proximal waist, an intermediate portion having a second outer diameter greater than the first outer diameter, and a distal waist;
- a pusher wire slidably disposed within the lumen of the sheath; and
- a locking element having a proximal end, a distal end, and an intermediate region disposed between the proximal end and the distal end, and a lumen extending from the proximal end to the distal end, the lumen of the locking element having a generally hourglass shape including a smaller inner diameter adjacent the intermediate region than at the proximal or distal end;
- wherein the locking element is configured to freely slide over a region of the sheath having the first outer diameter; and
- wherein when the locking element is disposed over the enlarged outer diameter region of the sheath having the second outer diameter, the distal end of the sheath extends distally of the distal end of the locking element and the locking element is configured to depress the sheath such that an inner surface of the sheath is depressed radially inwards and frictionally engages an outer surface of the pusher wire.

12. The medical device system of claim 11, wherein a cross-sectional shape of the lumen of the locking element is a same shape along a length of the lumen.

13. The medical device system of claim 11, wherein a cross-sectional shape of the lumen of the locking element varies along a length of the lumen.

14. The medical device system of claim 11, wherein the locking element is formed from a more rigid material than the sheath.

15. The medical device system of claim 11, further comprising an implant releasably coupled to the pusher wire.

* * * * *